US008465756B2

(12) United States Patent
Liu et al.

(10) Patent No.: US 8,465,756 B2
(45) Date of Patent: Jun. 18, 2013

(54) IMMUNOGENIC PEPTIDES OF TUMOR ASSOCIATED ANTIGEN L6 AND USES THEREOF IN CANCER THERAPY

(75) Inventors: Shih-Jen Liu, Miaoli County (TW); Hsin-Wei Chen, Miaoli County (TW); Pele Choi-Sing Chong, Miaoli County (TW); Chih-Hsiang Leng, Miaoli County (TW)

(73) Assignee: National Health Research Institutes, Miaoli County (TW)

( * ) Notice: Subject to any disclaimer, the term of this patent is extended or adjusted under 35 U.S.C. 154(b) by 253 days.

(21) Appl. No.: 12/846,092

(22) Filed: Jul. 29, 2010

(65) Prior Publication Data
US 2011/0038894 A1 Feb. 17, 2011

Related U.S. Application Data

(60) Provisional application No. 61/233,229, filed on Aug. 12, 2009.

(51) Int. Cl.
*A61K 39/00* (2006.01)
*A61P 35/00* (2006.01)
*C07K 16/30* (2006.01)

(52) U.S. Cl.
USPC ............ 424/277.1; 530/324; 530/325

(58) Field of Classification Search
None
See application file for complete search history.

(56) References Cited

U.S. PATENT DOCUMENTS
5,597,707 A   1/1997  Marken et al.
5,840,839 A * 11/1998  Wang et al. .................. 530/325
5,922,566 A   7/1999  Bandman et al.

FOREIGN PATENT DOCUMENTS
WO  WO/0188088  * 11/2001

OTHER PUBLICATIONS

Minev et al., Insertion signal sequcne fused to minimal peptides elicits specific CD8+ T-cell responses and prolongs survival of thymoma-bearing mice, 1994, Cancer Research, vol. 54, p. 4155-4161.*
Alexander et al., The optimization of helpter T lymphocyte (HTL) function in vaccine development, 1998, Immunologic Research, vol. 18, No. 2, p. 79-92.*
Schirle et al., Combining computer algorithms with experimental approaches permits the rapid and accurate identification of T cell epitopes from defined antgens, 2001, Journal of Immunological Methods, vol. 257, p. 1-16.*
Andersen et al., Poor correspondence between predicted and experimental binding of peptides to class I MHC molecules, 2000, Tissue Antigens, vol. 55, p. 519-531.*
Alves et al. "EphA2 as Target of Anticancer Immunotherapy: Identification of HLA-A*0201—Restricted Epitopes" Cancer Research, 63:8476-8480 (2003).
Jaramillo et al. "Recognition of HLA-A2-restricted mammaglobin-A-derived epitopes by CD8+ cytotoxic T lymphocytes from breast cancer patients" Breast Cancer Research and Treatment 88:29-41 (2004).
Gnjatic et al. "CD8+ T cell responses against a dominant cryptic HLA-A2 epitope after NY-ESO-1 peptide immunication of caner patients" Immunology PNAS 99(18):11813-11818 (2002).

* cited by examiner

*Primary Examiner* — Hong Sang
*Assistant Examiner* — Michael D Allen
(74) *Attorney, Agent, or Firm* — Occhiuti Rohicek & Tsao LLP

(57) ABSTRACT

An immunopeptide containing a T cell epitope from the tumor associated antigen L6 (TAL6) and a nucleic acid encoding the immunopeptide are described herein. The immunopeptide or its encoding nucleic acid can be used as a component of an immune composition for enhancing immune response against cancer cells that express TAL6.

8 Claims, 4 Drawing Sheets

```
                              SEQUENCE LISTING

<160> NUMBER OF SEQ ID NOS: 47

<210> SEQ ID NO 1
<211> LENGTH: 9
<212> TYPE: PRT
<213> ORGANISM: Artificial sequence
<220> FEATURE:
<223> OTHER INFORMATION: Synthetic HLA-A2 restricted CTL epitope (9-17
      aa of TAL6)

<400> SEQUENCE: 1

Cys Ile Gly His Ser Leu Val Gly Leu
1               5

<210> SEQ ID NO 2
<211> LENGTH: 9
<212> TYPE: PRT
<213> ORGANISM: Artificial sequence
<220> FEATURE:
<223> OTHER INFORMATION: Synthetic HLA-A2 restricted CTL epitope (13-21
      aa of TAL6)

<400> SEQUENCE: 2

Ser Leu Val Gly Leu Ala Leu Leu Cys
1               5

<210> SEQ ID NO 3
<211> LENGTH: 9
<212> TYPE: PRT
<213> ORGANISM: Artificial sequence
<220> FEATURE:
<223> OTHER INFORMATION: Synthetic HLA-A2 restricted CTL epitope (18-26
      aa of TAL6)

<400> SEQUENCE: 3

Ala Leu Leu Cys Ile Ala Ala Asn Ile
1               5

<210> SEQ ID NO 4
<211> LENGTH: 9
<212> TYPE: PRT
<213> ORGANISM: Artificial sequence
<220> FEATURE:
<223> OTHER INFORMATION: Synthetic HLA-A2 restricted CTL epitope (58-66
      aa of TAL6)

<400> SEQUENCE: 4

Leu Leu Met Leu Leu Pro Ala Phe Val
1               5

<210> SEQ ID NO 5
<211> LENGTH: 9
<212> TYPE: PRT
<213> ORGANISM: Artificial sequence
<220> FEATURE:
<223> OTHER INFORMATION: Synthetic HLA-A2 restricted CTL epitope (60-68
      aa of TAL6)

<400> SEQUENCE: 5

Met Leu Leu Pro Ala Phe Val Phe Ile
1               5
```

```
<210> SEQ ID NO 6
<211> LENGTH: 9
<212> TYPE: PRT
<213> ORGANISM: Artificial sequence
<220> FEATURE:
<223> OTHER INFORMATION: Synthetic HLA-A2 restricted CTL epitope (89-97
      aa of TAL6)

<400> SEQUENCE: 6

Ala Met Leu Ser Ser Val Leu Ala Ala
1               5

<210> SEQ ID NO 7
<211> LENGTH: 9
<212> TYPE: PRT
<213> ORGANISM: Artificial sequence
<220> FEATURE:
<223> OTHER INFORMATION: Synthetic HLA-A2 restricted CTL epitope (90-98
      aa of TAL6)

<400> SEQUENCE: 7

Met Leu Ser Ser Val Leu Ala Ala Leu
1               5

<210> SEQ ID NO 8
<211> LENGTH: 9
<212> TYPE: PRT
<213> ORGANISM: Artificial sequence
<220> FEATURE:
<223> OTHER INFORMATION: Synthetic HLA-A2 restricted CTL epitope (93-101
      aa of TAL6)

<400> SEQUENCE: 8

Ser Val Leu Ala Ala Leu Ile Gly Ile
1               5

<210> SEQ ID NO 9
<211> LENGTH: 9
<212> TYPE: PRT
<213> ORGANISM: Artificial sequence
<220> FEATURE:
<223> OTHER INFORMATION: Synthetic HLA-A2 restricted CTL epitope
      (114-122 aa of TAL6)

<400> SEQUENCE: 9

Gly Leu Ala Glu Gly Pro Leu Cys Leu
1               5

<210> SEQ ID NO 10
<211> LENGTH: 9
<212> TYPE: PRT
<213> ORGANISM: Artificial sequence
<220> FEATURE:
<223> OTHER INFORMATION: Synthetic HLA-A2 restricted CTL epitope
      (154-162 aa of TAL6)

<400> SEQUENCE: 10

His Ile Val Glu Trp Asn Val Ser Leu
1               5

<210> SEQ ID NO 11
<211> LENGTH: 9
<212> TYPE: PRT
<213> ORGANISM: Artificial sequence
<220> FEATURE:
<223> OTHER INFORMATION: Synthetic HLA-A2 restricted CTL epitope
      (164-172 aa of TAL6)

<400> SEQUENCE: 11
```

```
Ser Ile Leu Leu Ala Leu Gly Gly Ile
1               5
```

```
<210> SEQ ID NO 12
<211> LENGTH: 9
<212> TYPE: PRT
<213> ORGANISM: Artificial sequence
<220> FEATURE:
<223> OTHER INFORMATION: Synthetic HLA-A2 restricted CTL epitope
      (168-176 aa of TAL6)

<400> SEQUENCE: 12

Ala Leu Gly Gly Ile Glu Phe Ile Leu
1               5

<210> SEQ ID NO 13
<211> LENGTH: 9
<212> TYPE: PRT
<213> ORGANISM: Artificial sequence
<220> FEATURE:
<223> OTHER INFORMATION: Synthetic HLA-A2 restricted CTL epitope
      (181-189 aa of TAL6)

<400> SEQUENCE: 13

Val Ile Asn Gly Val Leu Gly Gly Ile
1               5

<210> SEQ ID NO 14
<211> LENGTH: 9
<212> TYPE: PRT
<213> ORGANISM: Artificial sequence
<220> FEATURE:
<223> OTHER INFORMATION: Synthetic HLA-A24 restricted CTL epitope (2-10
      aa of TAL6)

<400> SEQUENCE: 14

Cys Tyr Gly Lys Cys Ala Arg Cys Ile
1               5

<210> SEQ ID NO 15
<211> LENGTH: 9
<212> TYPE: PRT
<213> ORGANISM: Artificial sequence
<220> FEATURE:
<223> OTHER INFORMATION: Synthetic HLA-A24 restricted CTL epitope (12-20
      aa of TAL6)

<400> SEQUENCE: 15

His Ser Leu Val Gly Leu Ala Leu Leu
1               5

<210> SEQ ID NO 16
<211> LENGTH: 10
<212> TYPE: PRT
<213> ORGANISM: Artificial sequence
<220> FEATURE:
<223> OTHER INFORMATION: Synthetic HLA-A24 restricted CTL epitope (28-36
      aa of TAL6)

<400> SEQUENCE: 16

Leu Tyr Phe Pro Asn Gly Glu Thr Lys Tyr
1               5                   10

<210> SEQ ID NO 17
<211> LENGTH: 9
<212> TYPE: PRT
<213> ORGANISM: Artificial sequence
<220> FEATURE:
```

<223> OTHER INFORMATION: Synthetic HLA-A24 restricted CTL epitope (36-44
      aa of TAL6)

<400> SEQUENCE: 17

Lys Tyr Ala Ser Glu Asn His Leu Ser
1               5

<210> SEQ ID NO 18
<211> LENGTH: 9
<212> TYPE: PRT
<213> ORGANISM: Artificial sequence
<220> FEATURE:
<223> OTHER INFORMATION: Synthetic HLA-A24 restricted CTL epitope (45-53
      aa of TAL6)

<400> SEQUENCE: 18

Arg Phe Val Trp Phe Phe Ser Gly Ile
1               5

<210> SEQ ID NO 19
<211> LENGTH: 10
<212> TYPE: PRT
<213> ORGANISM: Artificial sequence
<220> FEATURE:
<223> OTHER INFORMATION: Synthetic HLA-A24 restricted CTL epitope (49-57
      aa of TAL6)

<400> SEQUENCE: 19

Phe Phe Ser Gly Ile Val Gly Gly Gly Leu
1               5                   10

<210> SEQ ID NO 20
<211> LENGTH: 9
<212> TYPE: PRT
<213> ORGANISM: Artificial sequence
<220> FEATURE:
<223> OTHER INFORMATION: Synthetic HLA-A24 restricted CTL epitope
      (105-113 aa of TAL6)

<400> SEQUENCE: 20

Gly Tyr Cys Val Ile Val Ala Ala Leu
1               5

<210> SEQ ID NO 21
<211> LENGTH: 10
<212> TYPE: PRT
<213> ORGANISM: Artificial sequence
<220> FEATURE:
<223> OTHER INFORMATION: Synthetic HLA-A24 restricted CTL epitope
      (131-140 aa of TAL6)

<400> SEQUENCE: 21

Thr Phe Ala Ser Thr Glu Gly Gln Tyr Leu
1               5                   10

<210> SEQ ID NO 22
<211> LENGTH: 9
<212> TYPE: PRT
<213> ORGANISM: Artificial sequence
<220> FEATURE:
<223> OTHER INFORMATION: Synthetic HLA-A24 restricted CTL epitope
      (138-147 aa of TAL6)

<400> SEQUENCE: 22

Gln Tyr Leu Leu Asp Thr Ser Thr Trp
1               5

<210> SEQ ID NO 23

```
<211> LENGTH: 9
<212> TYPE: PRT
<213> ORGANISM: Artificial sequence
<220> FEATURE:
<223> OTHER INFORMATION: Synthetic HLA-A24 restricted CTL epitope
      (157-165 aa of TAL6)

<400> SEQUENCE: 23

Glu Trp Asn Val Ser Leu Phe Ser Ile
1               5

<210> SEQ ID NO 24
<211> LENGTH: 14
<212> TYPE: PRT
<213> ORGANISM: Artificial sequence
<220> FEATURE:
<223> OTHER INFORMATION: Synthetic T helper-cell stimulating fragment

<400> SEQUENCE: 24

Gln Tyr Ile Lys Ala Asn Ser Lys Phe Ile Gly Ile Thr Glu
1               5                   10

<210> SEQ ID NO 25
<211> LENGTH: 10
<212> TYPE: PRT
<213> ORGANISM: Artificial sequence
<220> FEATURE:
<223> OTHER INFORMATION: Synthetic T helper-cell stimulating fragment

<400> SEQUENCE: 25

Ala Lys Phe Val Ala Ala Trp Thr Leu Lys
1               5                   10

<210> SEQ ID NO 26
<211> LENGTH: 17
<212> TYPE: PRT
<213> ORGANISM: Artificial sequence
<220> FEATURE:
<223> OTHER INFORMATION: Synthetic endoplasmic reticulum target sequence

<400> SEQUENCE: 26

Met Arg Tyr Met Ile Leu Gly Leu Leu Ala Leu Ala Ala Val Cys Ser
1               5                   10                  15

Ala

<210> SEQ ID NO 27
<211> LENGTH: 16
<212> TYPE: PRT
<213> ORGANISM: Artificial sequence
<220> FEATURE:
<223> OTHER INFORMATION: Synthetic endoplasmic reticulum target sequence

<400> SEQUENCE: 27

Arg Tyr Met Ile Leu Gly Leu Leu Ala Leu Ala Ala Val Cys Ser Ala
1               5                   10                  15

<210> SEQ ID NO 28
<211> LENGTH: 17
<212> TYPE: PRT
<213> ORGANISM: Artificial sequence
<220> FEATURE:
<223> OTHER INFORMATION: Synthetic endoplasmic reticulum target sequence

<400> SEQUENCE: 28

Met Arg Ala Ala Gly Ile Gly Ile Leu Thr Val Ala Ala Ala Ala
1               5                   10                  15

Gly
```

<210> SEQ ID NO 29
<211> LENGTH: 17
<212> TYPE: PRT
<213> ORGANISM: Artificial sequence
<220> FEATURE:
<223> OTHER INFORMATION: Synthetic endoplasmic reticulum target sequence

<400> SEQUENCE: 29

Met Ala Gly Ile Leu Gly Phe Val Phe Thr Leu Ala Ala Ala Ala
1               5                   10                  15

Gly

<210> SEQ ID NO 30
<211> LENGTH: 202
<212> TYPE: PRT
<213> ORGANISM: Homo sapiens

<400> SEQUENCE: 30

Met Cys Tyr Gly Lys Cys Ala Arg Cys Ile Gly His Ser Leu Val Gly
1               5                   10                  15

Leu Ala Leu Leu Cys Ile Ala Ala Asn Ile Leu Leu Tyr Phe Pro Asn
            20                  25                  30

Gly Glu Thr Lys Tyr Ala Ser Glu Asn His Leu Ser Arg Phe Val Trp
        35                  40                  45

Phe Phe Ser Gly Ile Val Gly Gly Leu Leu Met Leu Leu Pro Ala
    50                  55                  60

Phe Val Phe Ile Gly Leu Glu Gln Asp Asp Cys Cys Gly Cys Cys Gly
65                  70                  75                  80

His Glu Asn Cys Gly Lys Arg Cys Ala Met Leu Ser Ser Val Leu Ala
                85                  90                  95

Ala Leu Ile Gly Ile Ala Gly Ser Gly Tyr Cys Val Ile Val Ala Ala
            100                 105                 110

Leu Gly Leu Ala Glu Gly Pro Leu Cys Leu Asp Ser Leu Gly Gln Trp
        115                 120                 125

Asn Tyr Thr Phe Ala Ser Thr Glu Gly Gln Tyr Leu Leu Asp Thr Ser
    130                 135                 140

Thr Trp Ser Glu Cys Thr Glu Pro Lys His Ile Val Glu Trp Asn Val
145                 150                 155                 160

Ser Leu Phe Ser Ile Leu Leu Ala Leu Gly Gly Ile Glu Phe Ile Leu
                165                 170                 175

Cys Leu Ile Gln Val Ile Asn Gly Val Leu Gly Gly Ile Cys Gly Phe
            180                 185                 190

Cys Cys Ser His Gln Gln Gln Tyr Asp Cys
        195                 200

<210> SEQ ID NO 31
<211> LENGTH: 9
<212> TYPE: PRT
<213> ORGANISM: Artificial sequence
<220> FEATURE:
<223> OTHER INFORMATION: Synthetic HLA-A2 restricted CTL epitope (53-61
      aa of TAL6)

<400> SEQUENCE: 31

Ile Val Gly Gly Gly Leu Leu Met Leu
1               5

<210> SEQ ID NO 32
<211> LENGTH: 9

```
<212> TYPE: PRT
<213> ORGANISM: Artificial sequence
<220> FEATURE:
<223> OTHER INFORMATION: Synthetic HLA-A2 restricted CTL epitope
      (161-169 aa of TAL6)

<400> SEQUENCE: 32

Ser Leu Phe Ser Ile Leu Leu Ala Leu
1               5

<210> SEQ ID NO 33
<211> LENGTH: 9
<212> TYPE: PRT
<213> ORGANISM: Artificial sequence
<220> FEATURE:
<223> OTHER INFORMATION: Synthetic HLA-A2 restricted CTL epitope
      (177-185 aa of TAL6)

<400> SEQUENCE: 33

Cys Leu Ile Gln Val Ile Asn Gly Val
1               5

<210> SEQ ID NO 34
<211> LENGTH: 12
<212> TYPE: PRT
<213> ORGANISM: Artificial sequence
<220> FEATURE:
<223> OTHER INFORMATION: Synthetic PADRE peptide

<400> SEQUENCE: 34

Ala Lys Phe Val Ala Ala Trp Thr Leu Lys Ala Ala
1               5                   10

<210> SEQ ID NO 35
<211> LENGTH: 9
<212> TYPE: PRT
<213> ORGANISM: Artificial sequence
<220> FEATURE:
<223> OTHER INFORMATION: Synthetic EBV-derived HLA-A2-restricted epitope

<400> SEQUENCE: 35

Gly Leu Cys Thr Leu Val Ala Met Leu
1               5

<210> SEQ ID NO 36
<211> LENGTH: 12
<212> TYPE: PRT
<213> ORGANISM: Artificial sequence
<220> FEATURE:
<223> OTHER INFORMATION: Synthetic EBV-derived HLA-A2-restricted epitope

<400> SEQUENCE: 36

Gly Leu Cys Thr Leu Val Ala Met Leu Gly Leu Cys
1               5                   10

<210> SEQ ID NO 37
<211> LENGTH: 9
<212> TYPE: PRT
<213> ORGANISM: Artificial sequence
<220> FEATURE:
<223> OTHER INFORMATION: Synthetic EBV-derived HLA-A24-restricted
      epitope

<400> SEQUENCE: 37

Thr Tyr Gly Pro Val Phe Met Cys Leu
1               5

<210> SEQ ID NO 38
```

```
<211> LENGTH: 12
<212> TYPE: PRT
<213> ORGANISM: Artificial sequence
<220> FEATURE:
<223> OTHER INFORMATION: Synthetic EBV-derived HLA-A24-restricted
      epitope

<400> SEQUENCE: 38

Thr Tyr Gly Pro Val Phe Met Cys Leu Thr Tyr Gly
1               5                   10

<210> SEQ ID NO 39
<211> LENGTH: 9
<212> TYPE: PRT
<213> ORGANISM: Artificial sequence
<220> FEATURE:
<223> OTHER INFORMATION: Synthetic HLA-A24 restricted CTL epitope (22-30
      aa of TAL6)

<400> SEQUENCE: 39

Ile Ala Ala Asn Ile Leu Leu Tyr Phe
1               5

<210> SEQ ID NO 40
<211> LENGTH: 9
<212> TYPE: PRT
<213> ORGANISM: Artificial sequence
<220> FEATURE:
<223> OTHER INFORMATION: Synthetic HLA-A24 restricted CTL epitope
      (131-139 aa of TAL6)

<400> SEQUENCE: 40

Thr Phe Ala Ser Thr Glu Gly Gln Tyr
1               5

<210> SEQ ID NO 41
<211> LENGTH: 9
<212> TYPE: PRT
<213> ORGANISM: Artificial sequence
<220> FEATURE:
<223> OTHER INFORMATION: Synthetic HLA-A24 restricted CTL epitope
      (155-163 aa of TAL6)

<400> SEQUENCE: 41

Ile Val Glu Trp Asn Val Ser Leu Phe
1               5

<210> SEQ ID NO 42
<211> LENGTH: 10
<212> TYPE: PRT
<213> ORGANISM: Artificial sequence
<220> FEATURE:
<223> OTHER INFORMATION: Synthetic HLA-A24 restricted CTL epitope
      (157-166 aa of TAL6)

<400> SEQUENCE: 42

Glu Trp Asn Val Ser Leu Phe Ser Ile Leu
1               5                   10

<210> SEQ ID NO 43
<211> LENGTH: 9
<212> TYPE: PRT
<213> ORGANISM: Artificial sequence
<220> FEATURE:
<223> OTHER INFORMATION: Synthetic HLA-A24 restricted CTL epitope
      (170-178 aa of TAL6)

<400> SEQUENCE: 43

Gly Gly Ile Glu Phe Ile Leu Cys Leu
```

```
<210> SEQ ID NO 44
<211> LENGTH: 10
<212> TYPE: PRT
<213> ORGANISM: Artificial sequence
<220> FEATURE:
<223> OTHER INFORMATION: Synthetic HLA-A24 restricted CTL epitope
      (170-179 aa of TAL6)

<400> SEQUENCE: 44

Gly Gly Ile Glu Phe Ile Leu Cys Leu Ile
1               5                   10

<210> SEQ ID NO 45
<211> LENGTH: 10
<212> TYPE: PRT
<213> ORGANISM: Artificial sequence
<220> FEATURE:
<223> OTHER INFORMATION: Synthetic HLA-A24 restricted CTL epitope
      (154-163 aa of TAL6)

<400> SEQUENCE: 45

His Ile Val Glu Trp Asn Val Ser Leu Phe
1               5                   10

<210> SEQ ID NO 46
<211> LENGTH: 8
<212> TYPE: PRT
<213> ORGANISM: Artificial sequence
<220> FEATURE:
<223> OTHER INFORMATION: Synthetic peptide fragment from ovalbumin

<400> SEQUENCE: 46

Ser Ile Ile Asn Phe Glu Lys Leu
1               5

<210> SEQ ID NO 47
<211> LENGTH: 9
<212> TYPE: PRT
<213> ORGANISM: Artificial sequence
<220> FEATURE:
<223> OTHER INFORMATION: Synthetic peptide fragment from influenza
      viral M protein

<400> SEQUENCE: 47

Gly Ile Leu Gly Phe Val Phe Thr Leu
1               5
```

IMMUNOGENIC PEPTIDES OF TUMOR ASSOCIATED ANTIGEN L6 AND USES THEREOF IN CANCER THERAPY

RELATED APPLICATION

This application claims priority to U.S. Provisional Application No. 61/233,229, filed on Aug. 12, 2009, the content of which is incorporated herein by reference in its entirety.

BACKGROUND

The tumor-associated antigen L6 (TAL6), a member of the transmembrane-4 superfamily, is a tumor marker antigen expressed on various cancer cells, e.g., cells of lung cancer, breast cancer, colon cancer, and ovarine carcinoma. An anti-TAL6 antibody has been found to induce antibody-dependent cellular cytotoxicity against TAL6-expressing cancer cells and inhibit tumor growth in nude mice, indicating that TAL6 is a target antigen for cancer immunotherapy.

Cytotoxic T lymphocyte (CTL) epitope-based cancer vaccine is a promising anti-cancer drug. Containing a CTL-epitope from a tumor target antigen, this type of cancer vaccine induces cytotoxicity responses against tumor cells expressing the target antigen and thereby results in elimination of the tumor cells. Identification of CTL-epitopes from a tumor target antigen is essential to development of a CTL epitope-based cancer vaccine.

SUMMARY OF THE INVENTION

In one aspect, the present invention features an isolated immunopeptide that has a maximum length of 50 amino acids and includes the amino acid sequence of a T-cell epitope from the tumor associated antigen L6 (TAL6), or a nucleic acid encoding such an immunopeptide.

The term "isolated peptide" used herein refers to a peptide substantially free from naturally associated molecules, i.e., the naturally associated molecules constituting at most 20% by dry weight of a preparation containing the peptide. Purity can be measured by any appropriate method, e.g., column chromatography, polyacrylamide gel electrophoresis, and HPLC.

In one example, this immunopeptide contains a T-cell epitope restricted to HLA-A2, e.g., CIGHSLVGL (SEQ ID NO:1), SLVGLALLC (SEQ ID NO:2), ALLCIAANI (SEQ ID NO:3), LLMLLPAFV (SEQ ID NO:4), MLLPAFVFI (SEQ ID NO:5), AMLSSVLAA (SEQ ID NO:6), MLSSVLAAL (SEQ ID NO:7), SVLAALIGI (SEQ ID NO:8), GLAEGPLCL (SEQ ID NO:9), HIVEWNVSL (SEQ ID NO:10), SILLALGGI (SEQ ID NO:11), ALGGIEFIL (SEQ ID NO:12), or VINGVLGGI (SEQ ID NO:13). In another example, the immunopeptide contains a T-cell epitope restricted to HLA-A24, e.g., CYGKCARCI (SEQ ID NO:14), HSLVGLALL (SEQ ID NO:15), LYFPNGETKY (SEQ ID NO:16), KYASENHLS (SEQ ID NO:17), RFVWFFSGI (SEQ ID NO:18), FFSGIVGGGL (SEQ ID NO:19), GYCVIVAAL (SEQ ID NO:20), TFASTEGQYL (SEQ ID NO:21), QYLLDTSTW (SEQ ID NO:22), and EWNVSLFSI (SEQ ID NO:23).

In addition to a TAL6-derived T-cell epitope, the immunopeptide of this invention can further include a T helper-cell stimulating fragment, such as QYIKANSKFIGITE (SEQ ID NO:24) or AKFVAAWTLK (SEQ ID NO:25), and/or an endoplasmic reticulum target sequence (e.g., MRYMILGLLALAAVCSA; SEQ ID NO:26).

In another aspect, the present invention features an immunogenic composition containing any of the immunopeptides described above, a pharmaceutically acceptable carrier, and optionally, an adjuvant. The immunogenic composition can be used for treating cancer (e.g., lung cancer, breast cancer, colon cancer, or ovarian cancer) or for enhancing an immune response against TAL6.

In yet another aspect, this invention features an antibody specifically binding to a TAL6 fragment having the amino acid sequence selected from the group consisting of CIGHSLVGL (SEQ ID NO:1), SLVGLALLC (SEQ ID NO:2), ALLCIAANI (SEQ ID NO:3), LLMLLPAFV (SEQ ID NO:4), MLLPAFVFI (SEQ ID NO:5), AMLSSVLAA (SEQ ID NO:6), MLSSVLAAL (SEQ ID NO:7), SVLAALIGI (SEQ ID NO:8), GLAEGPLCL (SEQ ID NO:9), HIVEWNVSL (SEQ ID NO:10), SILLALGGI (SEQ ID NO:11), ALGGIEFIL (SEQ ID NO:12), VINGVLGGI (SEQ ID NO:13), CYGKCARCI (SEQ ID NO:14), HSLVGLALL (SEQ ID NO:15), LYFPNGETKY (SEQ ID NO:16), KYASENHLS (SEQ ID NO:17), RFVWFFSGI (SEQ ID NO:18), FFSGIVGGGL (SEQ ID NO:19), GYCVIVAAL (SEQ ID NO:20), TFASTEGQYL (SEQ ID NO:21), QYLLDTSTW (SEQ ID NO:22), and EWNVSLFSI (SEQ ID NO:23).

Also within the scope of this invention are (1) a pharmaceutical composition for use in treating cancer or enhancing immune responses against TAL6, the pharmaceutical composition containing any of the immunopeptides described above or an expression vector for producing the peptide, and (2) use of the immunogenic peptide or an expression vector for producing it in manufacturing a medicament for the intended purposes.

The details of one or more embodiments of the invention are set forth in the description below. Other features or advantages of the present invention will be apparent from the following drawings and detailed description of several embodiments, and also from the appended claims.

BRIEF DESCRIPTION OF THE DRAWINGS

The drawings are first described.

DETAILED DESCRIPTION OF THE INVENTION

Figure 1:
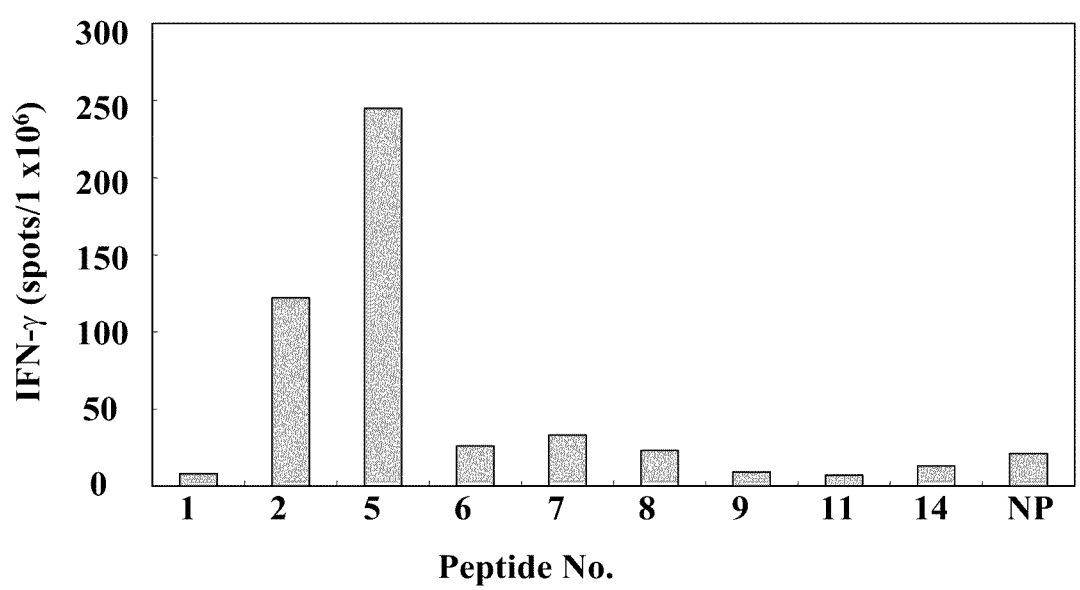
FIG. 1 is a chart showing induction of interferon γ in spleen cells from HLA-A2 transgenic mice immunized with a number of immunogenic peptides from TAL6: peptides 1 (SEQ ID NO:1), 2 (SEQ ID NO:2), 5 (SEQ ID NO:4), 6 (SEQ ID NO:5), 7 (SEQ ID NO:6), 8 (SEQ ID NO:7), 9 (SEQ ID NO:8), 11 (SEQ ID NO: 10), and 14 (SEQ ID NO:12). "NP" refers to absence of any peptide.

This invention features an immunopeptide having up to 50 amino acid residues. The immunopeptide includes a T cell epitope (e.g., a CTL epitope) derived from TAL6 and is restricted to a particular HLA allele, e.g., HLA-A2 or HLA-A24. A T cell epitope refers to a peptide capable of activating a T cell and subsequently eliciting immune responses mediated by the activated T-cell. A CTL epitope refers to a peptide capable of activating a CTL (also known as Tc or killer T cell), which subsequently stimulates CTL response, i.e., inducing death of abnormal cells (e.g., virus-infected or tumor cells). A CTL epitope, typically including 8-11 amino acid residues, forms a complex with a particular MHC class I molecule (including a heavy chain and a β2 microglobulin) presented on the surface of an antigen-presenting cell. This complex, upon binding to a T cell receptor of a T cell (e.g., a CD8 T cell), activates the T cell and subsequently triggers CTL responses.

TAL6 is a well-known tumor target antigen expressed on various cancer cells. Its amino acid sequence is showing below (SEQ ID NO:30):

```
Met Cys Tyr Gly Lys Cys Ala Arg Cys Ile Gly His

Ser Leu Val Gly Leu Ala Leu Leu Cys Ile Ala Ala

Asn Ile Leu Leu Tyr Phe Pro Asn Gly Glu Thr Lys

Tyr Ala Ser Glu Asn His Leu Ser Arg Phe Val Trp

Phe Phe Ser Gly Ile Val Gly Gly Gly Leu Leu Met

Leu Leu Pro Ala Phe Val Phe Ile Gly Leu Glu Gln

Asp Asp Cys Cys Gly Cys Cys Gly His Glu Asn Cys

Gly Lys Arg Cys Ala Met Leu Ser Ser Val Leu Ala

Ala Leu Ile Gly Ile Ala Gly Ser Gly Tyr Cys Val

Ile Val Ala Ala Leu Gly Leu Ala Glu Gly Pro Leu

Cys Leu Asp Ser Leu Gly Gln Trp Asn Tyr Thr Phe

Ala Ser Thr Glu Gly Gln Tyr Leu Leu Asp Thr Ser

Thr Trp Ser Glu Cys Thr Glu Pro Lys His Ile Val

Glu Trp Asn Val Ser Leu Phe Ser Ile Leu Leu Ala

Leu Gly Gly Ile Glu Phe Ile Leu Cys Leu Ile Gln

Val Ile Asn Gly Val Leu Gly Gly Ile Cys Gly Phe

Cys Cys Ser His Gln Gln Gln Tyr Asp Cys
```

T cell epitopes derived from TAL6 can be identified as follows. Peptides (e.g., containing 8-12 amino acids), spanning the whole amino acid sequence of TAL6, can be prepared via a conventional method, e.g., chemical synthesis. Their restriction to a particular HLA allele can be determined by assays known in the art. In one example, an MHC-peptide complex formation assay is performed as follows to determine the HLA class I restriction of a TAL6 peptide. A heavy chain encoded by an HLA class I allele (e.g., HLA-A2 or HLA-A24) and β2-microglobulin are expressed and purified. They are then mixed with one of the peptides mentioned above and any MHC-peptide complex thus formed can be detected by, e.g., ELISA. It is well known that a heavy chain encoded by a particular HLA class I allele forms stable complex with β2 microglobulin only in the presence of a peptide restricted to that HLA class allele. Therefore, the formation of the MHC-peptide complex indicates that the peptide contains an epitope restricted to the HLA class I allele.

After a TAL6 peptide is determined to be restricted to a particular HLA class I allele, it can then be subjected to in vitro or in vivo assays to confirm whether it contains a T cell epitope (e.g., a CTL epitope). Below is an example of an in vitro assay. A human carrying the HLA class I allele is identified by genotyping using methods known in the art. His or her peripheral blood mononuclear cells (PBMC) are collected and exposed to the peptide in the presence of autologous antigen presenting cells. If the peptide activates the PBMCs, it indicates that the epitope included therein is a T cell epitope restricted to the HLA class I allele. In another example, an in vivo assay described below is employed to determine whether the peptide includes a T cell epitope. A transgenic mouse expressing the HLA class I allele is immunized with the peptide. Induction of immune responses (e.g., secretion of cytokines such as IFN-γ and IL-2 or induction of cytotoxicity) indicates that the peptide contains a T cell epitope restricted to the HLA class I allele.

The immunopeptide of this invention can further include a T helper cell-stimulating fragment, e.g., QYIKANSKFIG-ITE (tetanus toxoid 830-843; SEQ ID NO:24) or AKFVAAWTLK (the PADRE peptide; SEQ ID NO:25). Alternatively or in addition, it can further include an endoplasmic reticulum target sequence. This target sequence facilitates entrance of a polypeptide containing it into the class I antigen presentation pathway, in which T-cell epitopes of the polypeptide form complexes with HLA class I molecules. Examples of the target sequence include the peptides MRYMILGLLALAAVCSA (SEQ ID NO:26) and RYMILGLLALAAVCSA (SEQ ID NO:27), both derived from adenovirus E3 protein. Other target sequences include, but are not limited to, peptide MRAAGIGILTVAAAAAG (SEQ ID NO:28; see Minev et al. 2000, *Eur J Immunol.* 30(8):2115-24.) and peptide MAGILGFVFTLAAAAAG (SEQ ID NO:29; see Gueguen, et al., 1994, *J Exp Med.* 1994, 180(5):1989-94).

The immunopeptide of the invention can be obtained by a conventional method, e.g., chemical synthesis or recombinant technology. To prepare a recombinant peptide, a nucleic acid encoding it can be linked to another nucleic acid encoding a fusion partner, e.g., Glutathione-S-Transferase (GST), 6×-His tag, or M13 Gene 3 protein. The resultant fusion nucleic acid expresses in suitable host cells a fusion protein that can be isolated by methods known in the art. The isolated fusion protein can be further treated, e.g., by enzymatic digestion, to remove the fusion partner and obtain the recombinant immunopeptide of this invention. As this immunopeptide contains a T-cell epitope derived from TAL6, a cancer marker antigen, it can be used for enhancing immune responses (e.g., CTL responses) against cancer, e.g., lung cancer, colon cancer, breast cancer, ovarian carcinoma, gastric cancer, Kaposi's sarcoma, and hepatoma. Upon administration to a subject, preferably carrying HLA-A2, HLA-A24, or an equivalent HLA allele, this composition is effective in treating cancer. An equivalent HLA allele of HLA-A2 or HLA-A24 is an allele that cross-reacts with a peptide restricted to HLA-A2 or HLA-A24. Examples include, but are not limited to, HLA-A3 and HLA-A11.

To treat cancer or enhancing immune responses against TAL6 in a subject in need thereof, any of the immunopeptides described above or an expression vector capable of expressing the immunopeptide can be mixed with a pharmaceutically acceptable carrier to form an immunogenic composition (e.g., a vaccine).

The immunopeptides may first require chemical modification since they may not have a sufficiently long half-life. A chemically modified peptide or a peptide analog includes any functional chemical equivalent of the peptide characterized by its increased stability and/or efficacy in vivo or in vitro in respect of the practice of the invention. The term peptide analog also refers to any amino acid derivative of a peptide as described herein. A peptide analog can be produced by procedures that include, but are not limited to, modifications to side chains, incorporation of unnatural amino acids and/or their derivatives during peptide synthesis and the use of cross-linkers and other methods that impose conformational constraint on the peptides or their analogs. Examples of side chain modifications include modification of amino groups, such as by reductive alkylation by reaction with an aldehyde followed by reduction with $NaBH_4$; amidation with methylacetimidate; acetylation with acetic anhydride; carbamylation of amino groups with cyanate; trinitrobenzylation of amino groups with 2, 4, 6, trinitrobenzene sulfonic acid (TNBS); alkylation of amino groups with succinic anhydride and tetrahydrophthalic anhydride; and pyridoxylation of lysine with pyridoxa-5'-phosphate followed by reduction with $NABH_4$. The guanidino group of arginine residues may be modified by the formation of heterocyclic condensation products with reagents such as 2,3-butanedione, phenylglyoxal and glyoxal. The carboxyl group may be modified by carbodiimide activation via o-acylisourea formation followed by subsequent derivatization, for example, to a corresponding amide. Sulfhydryl groups may be modified by methods, such as carboxymethylation with iodoacetic acid or iodoacetamide; performic acid oxidation to cysteic acid; formation of mixed disulphides with other thiol compounds; reaction with maleimide; maleic anhydride or other substituted maleimide; formation of mercurial derivatives using 4-chloromercuribenzoate, 4-chloromercuriphenylsulfonic acid, phenylmercury chloride, 2-chloromercuric-4-nitrophenol and other mercurials; carbamylation with cyanate at alkaline pH. Tryptophan residues may be modified by, for example, oxidation with N-bromosuccinimide or alkylation of the indole ring with 2-hydroxy-5-nitrobenzyl bromide or sulphonyl halides. Tryosine residues may be altered by nitration with tetranitromethane to form a 3-nitrotyrosine derivative. Modification of the imidazole ring of a histidine residue may be accomplished by alkylation with iodoacetic acid derivatives or N-carbethoxylation with diethylpyrocarbonate. Examples of incorporating unnatural amino acids and derivatives during peptide synthesis include, but are not limited to, use of norleucine, 4-amino butyric acid, 4-amino-3-hydroxy-5-phenylpentanoic acid, 6-aminohexanoic acid, t-butylglycine, norvaline, phenylglycine, ornithine, sarcosine, 4-amino-3-hydroxy-6-methylheptanoic acid, 2-thienyl alanine and/or D-isomers of amino acids.

The composition mentioned above can be prepared via conventional methods. It contains the immunopeptide/expression vector of the invention, a pharmaceutically acceptable carrier such as a phosphate buffered saline, a bicarbonate solution, and/or an adjuvant. When the immunopeptide does not include a T helper cell-stimulating fragment described above, such a fragment can be included in the composition to enhance immune responses. The carrier is selected on the basis of the mode and route of administration, and standard pharmaceutical practice. Suitable pharmaceutical carriers and diluents, as well as pharmaceutical necessities for their use, are described in Remington's Pharmaceutical Sciences.

An adjuvant, e.g., a cholera toxin, *Escherichia coli* heat-labile enterotoxin (LT), liposome, immune-stimulating complex (ISCOM), or immunostimulatory sequences oligodeoxynucleotides (ISS-ODN), can also be included in a composition of the invention, if necessary. The composition can also include a polymer that facilitates in vivo delivery. See Audran R. et al. Vaccine 21:1250-5, 2003; and Denis-Mize et al. Cell Immunol., 225:12-20, 2003. In one example, the immunopeptide is a component of a multivalent composition of vaccine against cancer. This multivalent composition contains at least one immunopeptide described above, along with at least one protective antigen isolated from influenza virus, para-influenza virus 3, *Strentococcus pneumoniae, Branhamella (Moroxella) gatarhalis, Staphylococcus aureus*, or respiratory syncytial virus, in the presence or absence of adjuvant. In another example, the immunopeptide is formulated as a virosome, which contains functional viral envelope glycoproteins, such as influenza virus hemagglutinin (HA).

Methods for preparing vaccines are generally well known in the art, as exemplified by U.S. Pat. Nos. 4,601,903; 4,599,231; 4,599,230; and 4,596,792.

Vaccines may be prepared as injectables, as liquid solutions or emulsions. The immuopeptide of this invention may be mixed with physiologically acceptable and excipients compatible. Excipients may include, water, saline, dextrose, glycerol, ethanol, and combinations thereof. The vaccine may further contain minor amounts of auxiliary substances such as wetting or emulsifying agents, pH buffering agents, or an adjuvant to enhance the effectiveness of the vaccines. Methods of achieving adjuvant effect for the vaccine includes use of agents, such as aluminum hydroxide or phosphate (alum), commonly used as 0.05 to 0.1 percent solutions in phosphate buffered saline. Vaccines may be administered parenterally, by injection subcutaneously or intramuscularly. Alternatively, other modes of administration including suppositories and oral formulations may be desirable. For suppositories, binders and carriers may include, for example, polyalkalene glycols or triglycerides. Oral formulations may include normally employed incipients such as, for example, pharmaceutical grades of saccharine, cellulose, magnesium carbonate and the like. These compositions take the form of solutions, suspensions, tablets, pills, capsules, sustained release formulations or powders and contain 10-95% of the immunopeptide described herein.

The immunogenic composition described above can also be a dendritic cell-based vaccine, which contains dendritic cells pulsed with any of the immunopeptides described herein.

Methods for preparing dendritic cell-based vaccines are well known in the art. See Slingluff et al., Clin Cancer Res. 12:2342s-2345s, 2006; Buchsel et al. Clin J Oncol Nurs. 10:629-40, 2006; and Yamanaka et al., Expert Opin Biol Ther.7:645-9, 2007.

An effective amount of the composition is administered to a subject (e.g., a human) via a conventional route for treating cancer or enhancing immune responses against TAL6-expressing cells. Exemplary administration routes include, but are not limited to, oral, parenteral, inhalation spray, topical, rectal, nasal, buccal, vaginal, or via an implanted reservoir. The term "parenteral" as used herein includes subcutaneous, intracutaneous, intravenous, intramuscular, intraarticular, intraarterial, intrasynovial, intrasternal, intrathecal, intralesional, and intracranial injection or infusion techniques. The term "an effective amount" as used herein refers to the amount of each active agent required to confer therapeutic effect on the subject, either alone or in combination with one or more other active agents. Effective amounts vary, as recognized by those skilled in the art, depending on route of administration, excipient usage, and co-usage with other active agents. The quantity to be administered depends on the subject to be treated, including, for example, the capacity of the individual's immune system to synthesize antibodies, and if needed to produce a cell-mediated immune response. Precise amounts of active ingredient required to be administered depend on the judgment of the practitioner. However, suitable dosage ranges are readily determinable by one skilled in the art and may be of the order of micrograms of the polypeptide of this invention. Suitable regimes for initial administration and booster doses are also variable, but may include an initial administration followed by subsequent administrations. The dosage of the vaccine may also depend on the route of administration and varies according to the size of the host.

A cancer patient can be identified and administered the immunogenic composition described above. The dose of the composition depends, for example, on the particular immunopeptide, whether an adjuvant is co-administered with the immunopeptide, the type of adjuvant co-administered, the mode and frequency of administration, as can be determined by one skilled in the art. Administration is repeated, if necessary, as can be determined by one skilled in the art. For example, a priming dose can be followed by three booster doses at weekly intervals. A booster shot can be given at 4 to 8 weeks after the first immunization, and a second booster can be given at 8 to 12 weeks, using the same formulation. Sera or T-cells can be taken from the subject for testing the immune response elicited by the immunogenic composition described herein. Methods of assaying cytotoxic T cells against an antigen are well known in the art. Additional boosters can be given as needed. By varying the amount of the immunopeptide, the dose of the composition, and frequency of administration, the immunization protocol can be optimized for eliciting a maximal anti-cancer immune response.

The immunopeptide of this invention can also be used to generate antibodies in animals (for production of antibodies) or humans (for treatment of cancer). Methods of making monoclonal and polyclonal antibodies and fragments thereof in animals are known in the art. See, for example, Harlow and Lane, (1988) Antibodies: A Laboratory Manual, Cold Spring Harbor Laboratory, New York. The term "antibody" includes intact immuglobulin molecules, antigen-binding fragments thereof, such as Fab, F(ab')$_2$, Fv, and genetically engineered antibodies, such as chimeric antibody, humanized antibody, and single-chain antibody, and dAb (domain antibody; Ward, et. al. (1989) Nature, 341, 544). These antibodies can be used for detecting TAL6-expressing cancers or for cancer therapy.

In general, to produce antibodies against a peptide, the peptide can be coupled to a carrier protein, such as KLH, mixed with an adjuvant, and injected into a host animal.

Antibodies produced in the animal can then be purified by peptide affinity chromatography. Commonly employed host animals include rabbits, mice, guinea pigs, and rats. Various adjuvants that can be used to increase the immunological response depend on the host species and include Freund's adjuvant (complete and incomplete), mineral gels such as aluminum hydroxide, CpG, surface-active substances such as lysolecithin, pluronic polyols, polyanions, peptides, oil emulsions, keyhole limpet hemocyanin, and dinitrophenol. Useful human adjuvants include BCG (bacille Calmette-Guerin) and *Corynebacterium parvum*.

Polyclonal antibodies, heterogeneous populations of antibody molecules, are present in the sera of the immunized subjects. Monoclonal antibodies, homogeneous populations of antibodies to a polypeptide of this invention, can be prepared using standard hybridoma technology (see, for example, Kohler et al. (1975) Nature 256, 495; Kohler et al. (1976) Eur. J. Immunol. 6, 511; Kohler et al. (1976) Eur J Immunol 6, 292; and Hammerling et al. (1981) Monoclonal Antibodies and T Cell Hybridomas, Elsevier, N.Y.). In particular, monoclonal antibodies can be obtained by any technique that provides for the production of antibody molecules by continuous cell lines in culture such as described in Kohler et al. (1975) Nature 256, 495 and U.S. Pat. No. 4,376,110; the human B-cell hybridoma technique (Kosbor et al. (1983) Immunol Today 4, 72; Cole et al. (1983) Proc. Natl. Acad. Sci. USA 80, 2026, and the EBV-hybridoma technique (Cole et al. (1983) Monoclonal Antibodies and Cancer Therapy, Alan R. Liss, Inc., pp. 77-96). Such antibodies can be of any immunoglobulin class including IgG, IgM, IgE, IgA, IgD, and any subclass thereof. The hybridoma producing the monoclonal antibodies of the invention may be cultivated in vitro or in vivo. The ability to produce high titers of monoclonal antibodies in vivo makes it a particularly useful method of production.

In addition, techniques developed for the production of "chimeric antibodies" can be used. See, e.g., Morrison et al. (1984) Proc. Natl. Acad. Sci. USA 81, 6851; Neuberger et al. (1984) Nature 312, 604; and Takeda et al. (1984) Nature 314:452. A chimeric antibody is a molecule in which different portions are derived from different animal species, such as those having a variable region derived from a murine monoclonal antibody and a human immunoglobulin constant region. Alternatively, techniques described for the production of single chain antibodies (U.S. Pat. Nos. 4,946,778 and 4,704,692) can be adapted to produce a phage library of single chain Fv antibodies. Single chain antibodies are formed by linking the heavy and light chain fragments of the Fv region via an amino acid bridge. Moreover, antibody fragments can be generated by known techniques. For example, such fragments include, but are not limited to, F(ab')$_2$ fragments that can be produced by pepsin digestion of an antibody molecule, and Fab fragments that can be generated by reducing the disulfide bridges of F(ab')$_2$ fragments.

Antibodies can also be humanized by methods known in the art. For example, monoclonal antibodies with a desired binding specificity can be commercially humanized (Scotgene, Scotland; and Oxford Molecular, Palo Alto, Calif.). Fully human antibodies, such as those expressed in transgenic animals are also features of the invention (see, e.g., Green et al. (1994) Nature Genetics 7, 13; and U.S. Pat. Nos. 5,545,806 and 5,569,825).

This invention also features an isolated nucleic acid encoding the immunopeptide of this invention, including a vector allowing expression of the immunopeptide. Such a nucleic acid can be used, as a DNA vaccine, for immunization by administration of the nucleic acid directly to a subject via a live vector, such as *Salmonella*, BCG, adenovirus, poxvirus, vaccinia, or a non-viral vector. Immunization methods based on nucleic acids are well known in the art.

Without further elaboration, it is believed that one skilled in the art can, based on the above description, utilize the present invention to its fullest extent. The following specific examples are therefore, to be construed as merely illustrative, and not limitative of the remainder of the disclosure in any way whatsoever. All publications cited herein are incorporated by reference.

EXAMPLE 1

Identification of HLA-A2-Restricted T-Cell Epitopes from TAL6

The sixteen synthesized peptides listed in Table 1 below, all derived from TAL6, were prepared by chemical synthesis.

These peptides were subjected to the MHC-peptide complex formation assay described in U.S. patent application Ser. No. 12/235,872 to identify those that are T cell epitopes restricted to HLA-A2.

TABLE 1

TAL6 Peptides and Their Binding Activity to HLA-A2

| Peptide No. | Position in TAL6 | Sequence | Relative binding (%) |
|---|---|---|---|
| 1 | 9-17 | CIGHSLVGL (SEQ ID NO: 1) | 93.30 |
| 2 | 13-21 | SLVGLALLC (SEQ ID NO: 2) | 125.70 |
| 3 | 18-26 | ALLCIAANI (SEQ ID NO: 3) | 53.65 |
| 4 | 53-61 | IVGGGLLML (SEQ ID NO: 31) | 43.36 |
| 5 | 58-66 | LLMLLPAFV (SEQ ID NO: 4) | 134.34 |
| 6 | 60-68 | MLLPAFVFI (SEQ ID NO: 5) | 154.57 |
| 7 | 89-97 | AMLSSVLAA (SEQ ID NO: 6) | 114.88 |
| 8 | 90-98 | MLSSVLAAL (SEQ ID NO: 7) | 162.82 |
| 9 | 93-101 | SVLAALIGI (SEQ ID NO: 8) | 158.08 |
| 10 | 114-122 | GLAEGPLCL (SEQ ID NO: 9) | 72.42 |
| 11 | 154-162 | HIVEWNVSL (SEQ ID NO: 10) | 91.11 |
| 12 | 161-169 | SLFSILLAL (SEQ ID NO: 32) | 42.57 |
| 13 | 164-172 | SILLALGGI (SEQ ID NO: 11) | 51.79 |
| 14 | 168-176 | ALGGIEFIL (SEQ ID NO: 12) | 112.83 |
| 15 | 177-185 | CLIQVINGV (SEQ ID NO: 33) | 26.33 |
| 16 | 181-189 | VINGVLGGI (SEQ ID NO: 13) | 59.06 |

Briefly, His-tag fused human HLA-A2 heavy chain (His-HLA-A2) and His-Tag fused human β2-microglobulin (His-β2) were expressed in E. coli as His-Tag fusion proteins following the procedures described below. An expression vector encoding either fusion protein was introduced into E. coli BL2 (DE3). A transformant thus produced was incubated at 37° C. 0.1 mM isopropyl b-D-thiogalactopyranoside (IPTG) was added to the E. coli culture when its O.D. value reached 0.5. The E. coli cells were further cultured at 37° C. for 3-4 hours and then harvested by centrifugation at 6000 rpm for 20 minutes. The cell pellets were suspended in Buffer A containing 8 M urea, 20 mM HEPES (pH 8.0), and 50 mM NaCl, and then subjected to sonication. The sonicated cells were again centrifuged and the supernant thus formed was collected and loaded on a Ni-NTA-agarose column to purify His-HLA-A2 or His-β2.

His-A2, His-β2, and each of the peptides listed in Table 1 above (test peptide) or a positive control peptide were incubated together in a refolding buffer containing 100 mM Tris-Hcl (pH8), 400 mM L-arginine, 2 mM EDTA, 5 mM reduced glutathione, 0.5 mM oxidized glutathione at 4° C. for 72 hours. Formation of MHC-peptide complexes was determined as follows.

An ELISA plate coated with anti-HLA antibody W6/32 (HB-95; ATCC.) (50 µL at 5 mg/ml in 100 mM carbonate buffer, pH 9.6 at 4° C. overnight). The plate was blocked with 250 µl/well 5% w/v skim milk powder in PBS at room temperature for 2 hours, and then washed twice with 300 ul/well 0.05% Tween-20 (Sigma) in PBS. The complexes were diluted in a PBS solution containing 1% BSA and subsequently added to the antibody-coated plate. The plate was incubated for 2 hours at room temperature to allow the complexes to bind to the anti-HLA antibody. After incubation, the plate was washed twice and then added with 100 µl/well horseradish peroxidase (HRP) labeled rabbit antihuman β2-microtubolin antibody (DAKO, Japan; diluted at 1:2500 in a PBS solution containing 1% BSA). The plate was incubated at room temperature for 2 hours, washed six times with PBS/0.05% Tween 20, and then added with HRP-conjugated anti-rabbit antibodies (1:2000). After incubating at room temperature for one hour, the plate was added with 3,3'-5,5'-tetramethylbenzidine hydrogenperoxide (TMB, Sigma), incubated for 30 minutes, and levels of the color thus developed in each well were read at 450 nM using an ELISA reader. Intensities of the color indicate MHC-peptide formation rate of a peptide. Relative binding activity was determined based on the MHC-peptide formation rate of each test peptide versus that of the positive control peptide following the formula: Relative binding activity=(MHC-peptide formation rate of test peptide−MHC-peptide formation rate of blank control)/(MHC-formation rate of positive control peptide−MHC-peptide formation rate of blank control). The relative binding activity of each test peptide is shown in Table 1 above. Peptides having relative binding activity greater than 50% are T cell epitopes restricted to HLA-A2.

EXAMPLE 2

Immunization of HLA-A2 Transgenic Mice with HLA-A2-Restricted T-Cell Epitopes from TAL6

One mg of each of the peptides (test peptides) that were identified as HLA-A2-restricted T-cell epitopes in Examples 1 above and 1 mg of PADRE peptide (AKFVAAWTLKAAA; SEQ ID NO:25), both in 0.5 ml PBS, were mixed together with 0.5 mL incomplete Freund's adjuvant (IFA). An EBV-derived HLA-A2-restricted epitope, i.e., GLCTLVAML (GLC; SEQ ID NO:35), was used as a positive control and an EBV-derived HAL-A24-restricted epitope, i.e., TYG-PVFMCL (TYG; SEQ ID NO:37), was used as negative control. 100 µl of the mixture (containing 50 µg of a test peptide) was injected s.c. into the tail base of a HLA-A2 transgenic mouse, once every 7 days for two times. Spleen cells were harvested from the treated mice 7 days after the second injection and cultured in the presence of 10 µg/mL of the test peptide. The supernatant of the cell culture was subjected to an ELISpot assy to examine the amount of IFN-γ contained therein, which correlates to the activity of the test peptide for stimulating T cells. As shown in FIG. 1, a number of test peptides (e.g., peptides 2 and 5) induced IFN-γ secretion of T cells, indicating that they are HLA-A2 restricted T cell epitopes.

EXAMPLE 3

Identification of HLA-A24-Restricted T-cell Epitopes from TAL6

The TAL6 peptides listed in Table 2 below were subjected to MHC-peptide complex formation assay, following the procedures described in Example 1 above, to identify those that can form MHC complex with human HLA-A24 and β2-microglobulin. Results thus obtained were shown in Table 2 below. The peptides that have a relative binding activity greater than 50% are identified as TAL6 T cell epitopes restricted to HLA-A24.

TABLE 2

TAL6 Peptides and Their Binding Activity to HLA-A24

| Peptide No. | Position in TAL6 | Sequence | Relative binding (%) |
|---|---|---|---|
| 17 | 2-10 | CYGKCARCI (SEQ ID NO: 14) | 125.73 |
| 18 | 12-20 | HSLVGLALL (SEQ ID NO: 15) | 61.73 |
| 19 | 22-30 | IAANILLYF (SEQ ID NO: 39) | 0.00 |
| 20 | 28-36 | LYFPNGETKY (SEQ ID NO: 16) | 84.95 |
| 21 | 36-44 | KYASENHLS (SEQ ID NO: 17) | 64.59 |
| 22 | 45-53 | RFVWFFSGI (SEQ ID NO: 18) | 91.88 |
| 23 | 49-57 | FFSGIVGGGL (SEQ ID NO: 19) | 72.36 |
| 24 | 105-113 | GYCVIVAAL (SEQ ID NO: 20) | 117.78 |
| 25 | 131-139 | TFASTEGQY (SEQ ID NO: 40) | 49.24 |
| 26 | 131-140 | TFASTEGQYL (SEQ ID NO: 21) | 115.71 |
| 27 | 138-147 | QYLLDTSTW (SEQ ID NO: 22) | 110.75 |
| 28 | 154-163 | HIVEWNVSLF (SEQ ID NO: 45) | 28.03 |
| 29 | 155-163 | IVEWNVSLF (SEQ ID NO: 41) | 41.01 |
| 30 | 157-165 | EWNVSLFSI (SEQ ID NO: 23) | 74.01 |
| 31 | 157-166 | EWNVSLFSIL (SEQ ID NO: 42) | 22.24 |
| 32 | 170-178 | GGIEFILCL (SEQ ID NO: 43) | 25.29 |
| 33 | 170-179 | GGIEFILCLI (SEQ ID NO: 44) | 14.85 |

EXAMPLE 4

Immunization of HLA-A24 Transgenic Mice with HLA-A24-Restricted T-cell Epitopes from TAL6

Figure 2:
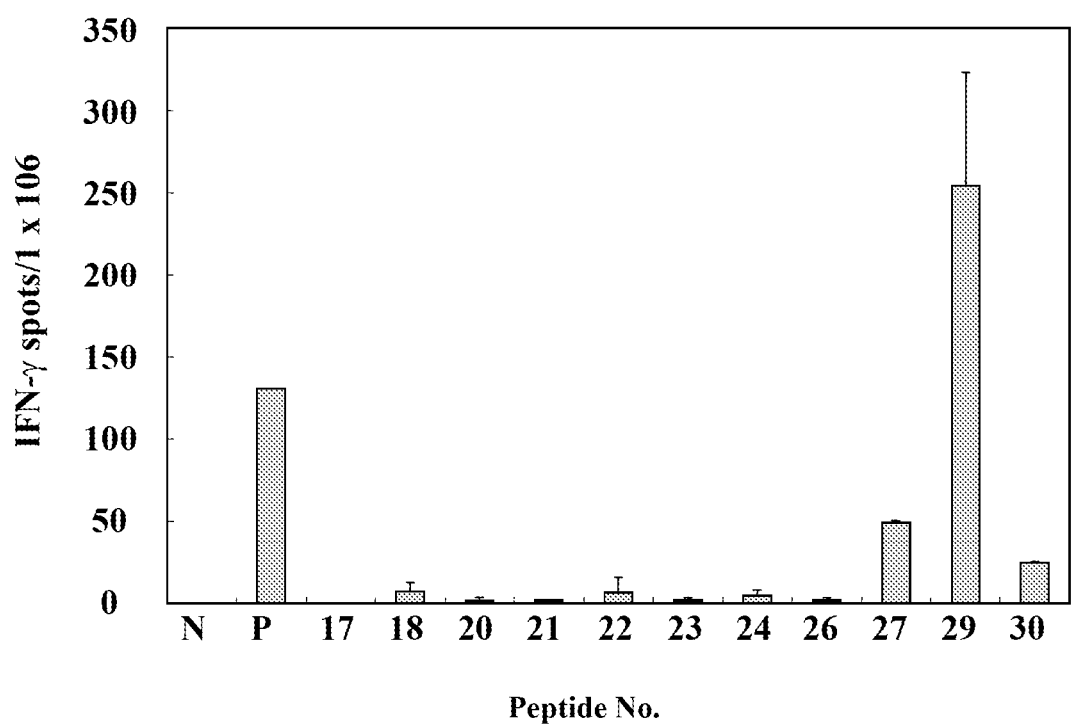
FIG. 2 is a chart showing induction of interferon γ in spleen cells from HLA-A24 transgenic mice immunized with a number of immunogenic peptides from TAL6: peptides 17 (SEQ ID NO:14), 18 (SEQ ID NO:15), 20 (SEQ ID NO:16), 21 (SEQ ID NO:17), 22 (SEQ ID NO:18), 23 (SEQ ID NO:19), 24 (SEQ ID NO:20), 26 (SEQ ID NO:21), 27 (SEQ ID NO:22), 29 (SEQ ID NO:41), and 30 (SEQ ID NO:23). "N" refers to a negative control and "P" refers to a positive control.

Each of the peptides (test peptides) that were identified as HLA-A24-restricted T-cell epitopes in Examples 3 above were used to immunize HAL-A24 transgenic mice, following the procedures described in Example 2 above. EBV peptides GLC and TYG were used as a negative control and a positive control, respectively. As shown in FIG. 2, a number of test peptides (e.g., peptides 27, 29, and 30) induced IFN-γ secretion of T cells, indicating that they are HAL-A24 restricted T cell epitopes.

EXAMPLE 5

Immunization of HLA-A2 Transgenic Mice with Expression Vectors Producing TAL6 Induced T-cell Responses Specific to TAL6 Peptides Expression plasmid pEK/TAL6, constructed via conventional recombinant technology using expression vector pCIneo (Promega, Madison, Wis., USA), was designed for expressing a fusion protein containing an endoplasmic reticulum targeting sequence, an H-2Kb-restricted sequence SIINFEKL (SEQ ID NO:46; derived from ovalbumin), an HLA-A2-restricted sequence GILGFVFTL (SEQ ID NO:47; derived from the M protein of the influenza virus), and TAL6.

Figure 3:
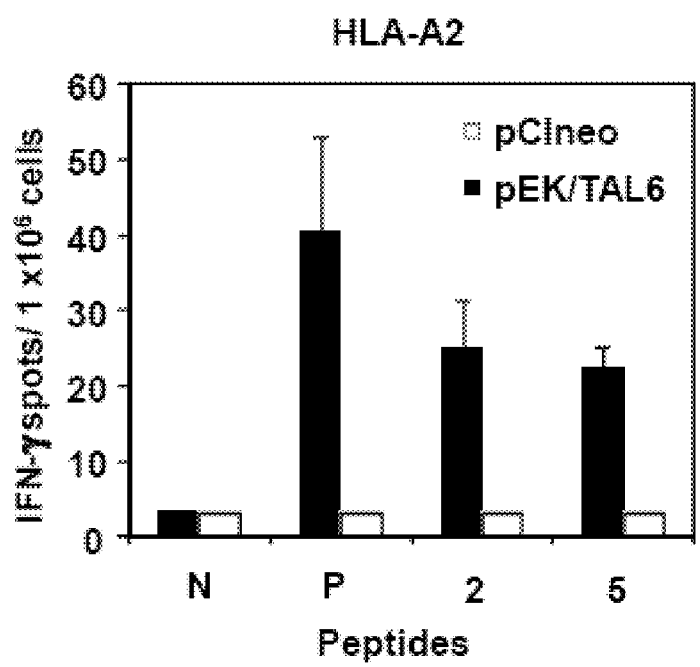
FIG. 3 is a chart showing induction of peptide-specific (i.e., peptide 2 (SEQ ID NO:2) and peptide 5 (SEQ ID NO:4) T-cell responses in plasmid pEK/TAL6 DNA immunized mice. An IFN-γ ELISpot assay was performed to detect IFN-γ-secreting cells. "N" refers to a negative control and "P" refers to a positive control.

Mice were immunized with pEK/TAL6 or pCIneo via intramuscular injection for 2-3 times during a 3-week period. Seven days after the final injection, the immunized mice were sacrificed, their splenocytes harvested and stimulated with various test TAL6 peptides. Presence of IFN-γ-secreting cells, which were activated by a test TAL6 peptide, was determined by IFN-γ ELISpot. As shown in FIG. 3, splenocytes from pEK/TAL6-immunized mice were responsive to Peptides 2 and 5 listed in Table 1 above. This result indicates that DNA vaccine expressing TAL6 induced T cell responses specific to certain TAL6 peptides.

EXAMPLE 6

Immunization with TAL6 Peptides Inhibited Tumor Growth in HLA-A2 Transgenic Mice Peptide 2 or Peptide 5 listed in Table 1 above, mixed with IFA, was administered subcutaneously to HLA-A2 transgenic mice (50 μg/mouse) or wild-type C57BL/6 mice twice in two weeks. Twenty-one days later, each of the immunized mice was transplanted subcutaneously with $2\times10^5$ of tumor cells EL4/TAL6/HLA-A2 (EL4 cells stably expressing both TAL6 and HLA-A2) to induce tumor growth in the immunized mice. Sizes of the tumors in the treated mice were monitored every 2-3 days. The tumor volume was calculated using the formula: tumor volume=length×width×width/2.

Figure 4:
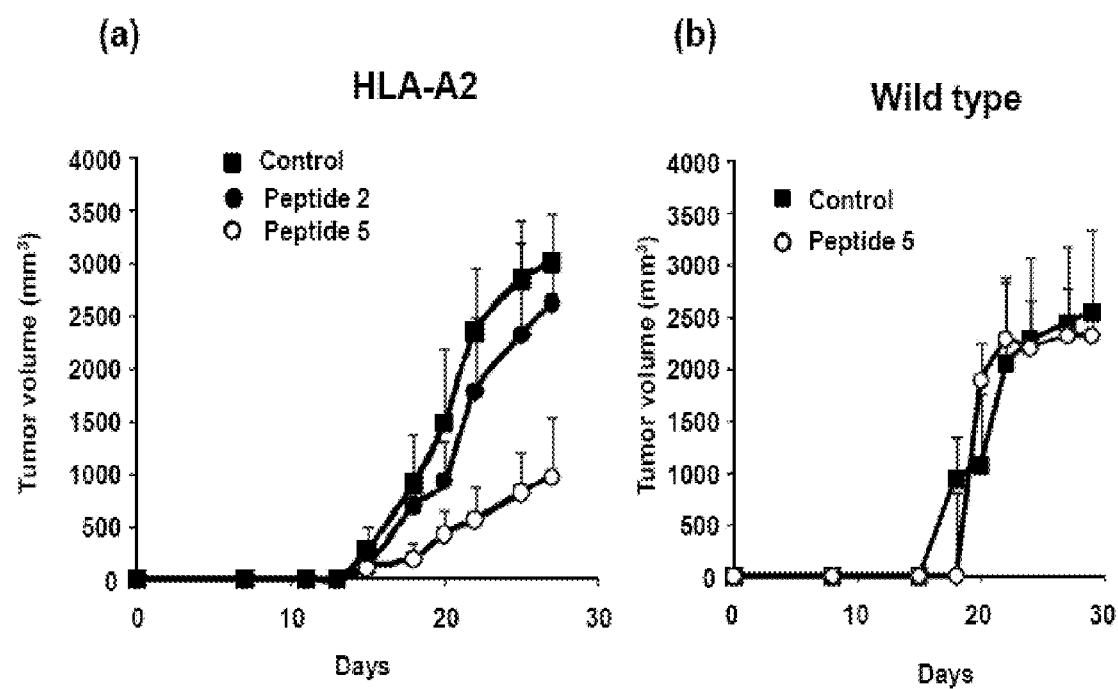
FIG. 4 is a chart showing inhibition of tumor growth in mice immunized by immunopeptides derived from TAL6. Tumor volume was calculated using the formula: tumor

Immunization of Peptide 5 significantly inhibited tumor growth in the HLA-A2 transgenic mice, but not in the wild-type mice. See FIG. 4. Immunization of Peptide 2 also reduced tumor growth in the HLA-A2 transgenic mice, albeit in a lower level. These results indicated that immunization with HLA-A2 restricted immunopeptides derived from TAL6 effectively inhibited tumor growth in HLA-A2 carriers.

OTHER EMBODIMENTS

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the claims.

What is claimed is:

1. An isolated immunopeptide, comprising the amino acid sequence of a T-cell epitope from the tumor associated antigen L6 (TAL6), wherein (i) the immunopeptide consists of the amino acid sequence of SEQ ID NO:2, or (ii) the T-cell epitope consists of the amino acid sequence of SEQ ID NO:4 and the immunopeptide has a maximum length of 50 amino acids.

2. The isolated immunopeptide of claim 1, wherein the T-cell epitope is restricted to HLA-A2.

3. The isolated immunopeptide of claim 1, further comprising an endoplasmic reticulum targeting sequence, wherein the T-cell epitope consists of the amino acid sequence of SEQ ID NO:4.

4. The isolated immunopeptide of claim 1, further comprising a T helper-cell stimulating fragment having the amino acid sequence of QYIKANSKFIGITE (SEQ ID NO:24) or AKFVAAWTLK (SEQ ID NO:25), wherein the T-cell epitope consists of the amino acid sequence of SEQ ID NO:4.

5. An immunogenic composition, comprising the immunopeptide of claim 1 and a pharmaceutically acceptable carrier.

6. The immunogenic composition of claim 5, further comprising an adjuvant.

7. The isolated immunopeptide of claim 1, consisting of the amino acid sequence of SEQ ID NO:2.

8. The isolated immunopeptide of claim 1, consisting of the amino acid sequence of SEQ ID NO:4.

* * * * *